United States Patent
Harvey et al.

(10) Patent No.: US 9,593,096 B2
(45) Date of Patent: Mar. 14, 2017

(54) α7 NICOTINIC ACETYLCHOLINE RECEPTOR MODULATORS AND USES THEREOF-III

(71) Applicant: Merck Sharp & Dohme Corp., Rahway, NJ (US)

(72) Inventors: Andrew Harvey, Thebarton (AU); Belinda Huff, Thebarton (AU); Rajinder Singh, Thebarton (AU); Nathan Kuchel, Thebarton (AU)

(73) Assignee: MERCK SHARP & DOHME CORP., Rahway, NJ (US)

(*) Notice: Subject to any disclaimer, the term of this patent is extended or adjusted under 35 U.S.C. 154(b) by 0 days.

(21) Appl. No.: 14/786,798

(22) PCT Filed: Apr. 24, 2014

(86) PCT No.: PCT/AU2014/050021
§ 371 (c)(1),
(2) Date: Oct. 23, 2015

(87) PCT Pub. No.: WO2014/172759
PCT Pub. Date: Oct. 30, 2014

(65) Prior Publication Data
US 2016/0075684 A1 Mar. 17, 2016

(30) Foreign Application Priority Data
Apr. 24, 2013 (AU) ................ 2013901443

(51) Int. Cl.
*A61K 31/4439* (2006.01)
*C07D 401/12* (2006.01)
*C07D 403/12* (2006.01)
*C07D 401/14* (2006.01)

(52) U.S. Cl.
CPC ......... *C07D 401/12* (2013.01); *C07D 401/14* (2013.01); *C07D 403/12* (2013.01)

(58) Field of Classification Search
CPC ..................... C07D 401/12; A61K 31/4439
USPC ........................... 514/339; 546/277.4
See application file for complete search history.

(56) References Cited

U.S. PATENT DOCUMENTS

2013/0211075 A1    8/2013  Ushio et al.

FOREIGN PATENT DOCUMENTS

FR    WO2012146318    11/2012

OTHER PUBLICATIONS

Duflos et al, Eur. J. Med. Chem. (2001), pp. 545-553.*
Boess, Novel a7 Nicotinic Acetylcholine Receptor Agonist, Journal of Pharmacology, Dec. 21, 2006, pp. 716-725, 321.
Dunlop, Old and New Pharmacology, Discovery Neuroscience, Sep. 25, 2008, 766-776, 328.
Mazurov et al, Discovery and Development of [alpha]7 Nicotinic Acetylcholine Receptor Modulators, Journal of Medicinal Chemistry, 2011, 7943-7961, vol. 54 Issue 23.

* cited by examiner

*Primary Examiner* — Kamal Saeed
*Assistant Examiner* — Janet L Coppins
(74) *Attorney, Agent, or Firm* — Matthew A. Leff; John C. Todaro

(57) ABSTRACT

The present invention relates to chemical compounds useful in the positive modulation of the alpha 7 nicotinic acetylcholine receptor (α7 nAChR).

4 Claims, No Drawings

α7 NICOTINIC ACETYLCHOLINE RECEPTOR MODULATORS AND USES THEREOF-III

CROSS REFERENCE TO RELATED APPLICATIONS

This application is a U.S. National Phase application under 35 U.S.C. §371 of PCT Application No. PCT/AU2014/050021, filed Apr. 24, 2014, which in turn claims the priority of Australian priority application serial no. AU2013901443 filed Apr. 24, 2013, which applications are incorporated herein in their entirety by reference thereto.

FIELD OF THE INVENTION

The present invention relates to chemical compounds useful in the positive modulation of the alpha 7 nicotinic acetylcholine receptor (α7 nAChR). The invention also relates to the use of these compounds in the treatment or prevention of a broad range of diseases in which the positive modulation of α7 nAChR is advantageous, including neurodegenerative and neuropsychiatric diseases and also inflammatory diseases.

BACKGROUND

The α7 nAChRs are rapidly desensitizing ligand-gated ion channels that are abundantly expressed in the cerebral cortex and the hippocampus, a limbic structure intimately linked to attention processing and memory formation. α7 nAChRs modulate neurotransmitter release and are responsible for direct fast excitatory neurotransmission. At the cellular level, activation of α7 nAChRs can regulate interneuron excitability, modulate the release of excitatory and inhibitory neurotransmitters, and contribute to neuroprotective effects.

Several lines of evidence indicate that impaired attention and cognition, which are characteristic of neurological and psychiatric disorders such as Alzheimer's disease (AD), schizophrenia, Parkinson's disease (PD), multiple sclerosis, attention deficit hyperactivity disorder (ADHD), mild cognitive impairment (MCI), age associated memory impairment (AAMI), may involve degeneration or hypo-function of cholinergic input. Moreover, genetic linkage has identified α7 AChRs as a predisposing factor related to sensory gating deficits. Thus, targeting the α7 nAChRs represents a therapeutic strategy for ameliorating cognitive deficits associated with neurodegenerative and neuropsychiatric diseases.

A number of reports also suggest that α7 nAChRs mediate protection against neurotoxicity induced by amyloid beta and excitotoxic insults. Peripherally, α7 nAChRs are expressed in macrophages and their stimulation is essential for inhibiting the release of proinflammatory cytokines (e.g. TNF-a, IL-1) via the cholinergic anti-inflammatory pathway which is triggered in response to signals from the vagus nerve. Thus, the clinical use of positive modulators of the α7 nAChRs could also represent a strategy against inflammatory diseases.

Selective positive allosteric modulation (PAM) of the α7 nAChR is a recently proposed therapeutic approach for treating these disease states. A key advantage of this approach is that modulation only occurs in the presence of endogenous agonist thereby preserving the temporal and spatial integrity of neurotransmission. Several different profiles have been described for PAMs of the α7 nAChR ranging from Type I modulators that predominately affect the peak current and may also increase channel affinity for the agonist, to Type II modulators that affect the peak current, delay the desensitization of the receptor and may reactivate desensitized receptors. Several PAMs have been described in the literature with some Type I examples including 5-Hydroxyindole, NS-1738, Ivermectin, Galantamine and Genistein; Type II examples including PNU-120596, TQS and A-867744 and some intermediate examples being SB-206553 and JNJ-1930942. All PAMs demonstrate enhanced receptor responses to the endogenous ligands acetylcholine and choline, as well as to nicotine and other agonists.

The present invention seeks to address some of the shortcomings of the prior art therapeutics and is directed to a new class of compounds which exhibit positive modulation of α7 nAChR.

SUMMARY OF THE INVENTION

In another aspect the invention provides compounds of formula (I) or salts thereof:

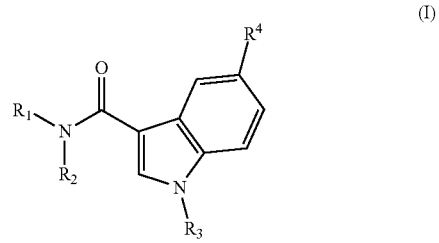

wherein
$R_1$ is an optionally substituted 6-membered N-containing heteroaryl;
$R_2$ is selected from hydrogen or $C_1$-$C_4$ alkyl;
$R_3$ is selected from optionally substituted $C_1$-$C_6$ alkyl, $C_3$-$C_6$ cycloalkyl, heterocyclyl, trifluoromethyl, difluoromethyl or optionally substituted aryl; and
$R_4$ is selected from F, Cl, $SO_2NRR'$ (when R and R' are independently hydrogen or $C_1$-$C_6$ alkyl), optionally substituted $C_1$-$C_6$ alkyl, optionally substituted $C_3$-$C_6$ cycloalkyl, optionally substituted $C_1$-$C_6$ alkoxy, halo $C_1$-$C_6$ alkyl, halo $C_1$-$C_6$ alkoxy, optionally substituted heteroaryl, optionally substituted heterocyclyl, or optionally substituted aryl, provided that the following compounds are excluded:

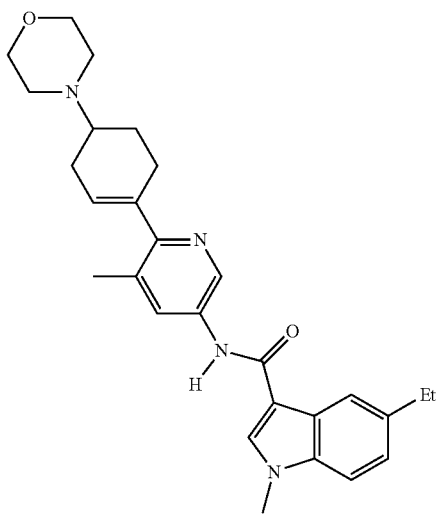

-continued

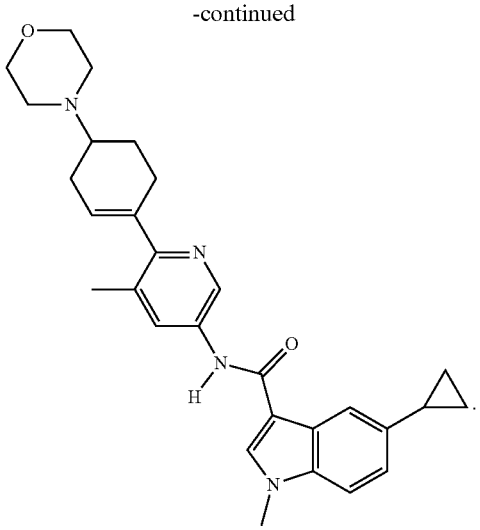

In an embodiment $R_1$ is an optionally substituted 6-membered N-containing heteroaryl selected from optionally substituted pyridine, optionally substituted pyrimidine, optionally substituted pyrazine, or optionally substituted pyridazine.

In an embodiment $R_1$ is a 6-membered N-containing heteroaryl selected from pyridine, pyrimidine, pyrazine, or pyridazine, each of which has been independently substituted one or two times with a group selected from F, halo $C_1$-$C_3$ alkyl, or halo $C_1$-$C_3$ alkoxy.

In an embodiment $R_1$ is an optionally substituted pyridine or optionally substituted pyrimidine.

In an embodiment $R_1$ is a pyridine or pyrimidine, each of which has been independently substituted one or two times with a group selected from F, halo $C_1$-$C_3$ alkyl, or halo $C_1$-$C_3$ alkoxy.

In a further aspect the invention provides compounds of formula (Ia) or salts thereof:

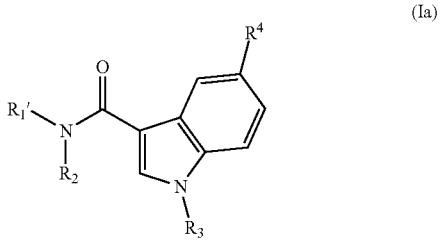

(Ia)

wherein
$R_1'$ is pyridine or pyrimidine, each of which has been independently substituted one or two times with a group selected from F, halo $C_1$-$C_3$ alkyl, or halo $C_1$-$C_3$ alkoxy;
$R_2$ is selected from hydrogen or $C_1$-$C_4$ alkyl;
$R_3$ is selected from optionally substituted $C_1$-$C_6$ alkyl, $C_3$-$C_6$ cycloalkyl, heterocyclyl, trifluoromethyl, difluoromethyl, or optionally substituted aryl; and
$R_4$ is selected from F, Cl, $SO_2NRR'$ (when R and R' are independently hydrogen or $C_1$-$C_6$ alkyl), optionally substituted $C_1$-$C_6$ alkyl, optionally substituted $C_3$-$C_6$ cycloalkyl, optionally substituted $C_1$-$C_6$ alkoxy, halo $C_1$-$C_6$ alkyl, halo $C_1$-$C_6$ alkoxy, optionally substituted heteroaryl, optionally substituted heterocyclyl, or optionally substituted aryl.

In another embodiment $R_1$ or $R_1'$ is selected from pyridine or pyrimidine, each of which is substituted with one of F or $CF_3$.

In another embodiment $R_4$ is selected from F, halo $C_1$-$C_6$ alkyl, or halo $C_1$-$C_6$ alkoxy.

Accordingly, in a further aspect the invention provides compounds of formula (Ib) or salts thereof:

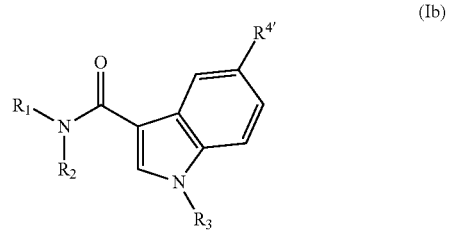

(Ib)

wherein
$R_1$ is an optionally substituted 6-membered N-containing heteroaryl;
$R_2$ is selected from hydrogen or $C_1$-$C_4$ alkyl;
$R_3$ is selected from optionally substituted $C_1$-$C_6$ alkyl, $C_3$-$C_6$ cycloalkyl, heterocyclyl, trifluoromethyl, difluoromethyl, or optionally substituted aryl; and
$R_4'$ is selected from F, halo $C_1$-$C_4$ alkyl or halo $C_1$-$C_6$ alkoxy.

In a further aspect the invention provides a method for the treatment or prevention of cognitive deficits associated with neurodegeneration or neuropsychiatric diseases, said method including the step of administering a compound of formula (I), (Ia), or (Ib), or a pharmaceutically acceptable salt thereof, or a composition comprising a compound of formula (I), (Ia), or (Ib), and related formulae as herein defined or a pharmaceutically acceptable salt thereof.

In still a further aspect the invention provides a method for the treatment or prevention of inflammatory diseases, said method including the step of administering a compound of formula (I), (Ia), or (Ib), and related formulae as herein defined or a pharmaceutically acceptable salt thereof, or a composition comprising a compound of formula (I), (Ia), or (Ib), and related formulae as herein defined or a pharmaceutically acceptable salt thereof.

In another aspect the invention provides the use of a compound of formula (I), (Ia), or (Ib), and related formulae as herein defined or a salt thereof in the manufacture of a medicament for the treatment or prevention of cognitive deficits associated with neurodegeneration or neuropsychiatric diseases.

In another aspect the invention provides the use of a compound of formula (I), (Ia), or (Ib), and related formulae as herein defined or a salt thereof in the manufacture of a medicament for the treatment or prevention of inflammatory diseases.

In another aspect of the invention there is provided a method of positively modulating α7nAChRs in a cell by contacting the cell with a compound of formula (I), (Ia), or (Ib), and related formulae as herein defined or a pharmaceutically acceptable salt thereof, to said cell.

In a further aspect of the invention there is provided a pharmaceutical composition for use as a neuroprotective agent, the composition comprising an effective amount of a compound of formula (I), (Ia), or (Ib), and related formulae as herein defined or a pharmaceutically acceptable salt thereof and optionally a carrier or diluent.

In still a further aspect of the invention there is provided a pharmaceutical composition for use as an anti-inflammatory agent, the composition comprising an effective amount of a compound of formula (I), (Ia), or (Ib), and related formulae as herein defined or a pharmaceutically acceptable salt thereof and optionally a carrier or diluent.

In another aspect of the invention there is provided a process for the preparation of compounds of formula (I), (Ia), or (Ib), and related formulae as herein defined or salts thereof.

DETAILED DESCRIPTION OF THE INVENTION

The term "alkyl" as used alone or in combination herein refers to a straight or branched chain saturated hydrocarbon group. The term "$C_{1-12}$ alkyl", for instance, refers to such a group containing from one to twelve carbon atoms and "lower alkyl" refers to $C_{1-6}$ alkyl groups containing from one to six carbon atoms, such as methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "$C_{3-6}$ cycloalkyl", for instance, refers to such a group having from 3 to 6 carbon atoms. Examples include cyclobutyl, cyclopentyl and cyclohexyl.

The term "alkenyl" refers to a straight or branched hydrocarbon containing one or more double bonds, preferably one or two double bonds. The term "$C_{2-12}$ alkenyl", for instance, refers to such a group containing from two to twelve carbon atoms. Examples of alkenyl include allyl, 1-methylvinyl, butenyl, iso-butenyl, 1, 3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. The term "$C_{2-12}$ alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

In certain embodiments the aryl group may be selected from phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$.

The term "halo alkoxy" group has one or more of the hydrogen atoms on an alkoxy group replaced with halogens. A notable example is —$OCF_3$.

The term "optionally substituted" means that a group may include one or more substituents. One or more hydrogen atoms on the group may be replaced by substituent groups independently selected from halogens (for example halo alkyl such as —$CF_3$), $C_{1-6}$ alkyl, $C_{2-6}$ alkenyl, $C_{2-6}$ alkynyl, —$(CH_2)_pC_{3-7}$cycloalkyl, —$(CH_2)_pC_{4-7}$cycloalkenyl, —$(CH_2)_p$ aryl, —$(CH_2)_p$ heterocyclyl, —$(CH_2)_p$ heteroaryl, —$C_6H_4S(O)_qC_{1-6}$ alkyl, —C(Ph)$_3$, —CN, —OR, —O—$(CH_2)_{1-6}$—R, —O—$(CH_2)_{1-6}$—OR, —OC(O)R, —C(O)R, —C(O)OR, —OC(O)NR'R'', —NR'R'', —NRC(O)R', —NRC(O)NR'R'', —NRC(S)NR'R'', —NRS(O)$_2$R', —NRC(O)OR', —C(NR)NR'R'', —C(=NOR')R, —C(=NOH)NR'R'', —C(O)NR'R'', —C(=NCN)—NR'R'', —C(=NR)NR'R'', —C(=NR')SR'', —NR'C(=NCN)SR'', —CONRSO$_2$R', —C(S)NR'R'', —S(O)$_q$R, —SO$_2$NR'R'', —SO$_2$NRC(O)R', —OS(O)$_2$R, —PO(OR)$_2$ and —NO$_2$;

where p is 0-6, q is 0-2 and each R, R' and R'' is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R'' are attached to the same nitrogen atom, they may, together with the atom to which they are attached, form a 5 to 7 membered nitrogen containing heterocyclic ring.

A list of preferred optional substituents includes: halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —P=O(OH)$NH_2$, —$S(O)_2NH_2$, —$S(O)_2NHC_{1-4}$alkyl, —$S(O)_2N(C_{1-4}$ alkyl$)_2$, $C_{1-6}$ alkylcarbonyl, $C_{1-6}$ alkoxycarbonyl, $CO_2H$, —S(O)R''', (where R''' is lower alkyl or cycloalkyl) and —$S(O)_2R''''$ (where R'''' is lower alkyl, cycloalkyl or OH).

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, aryl, heteroaryl or heterocyclyl group, the group may itself be optionally substituted with one to six of the same or different substituents selected from halogen, $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —P=O(OH)$NH_2$, —$S(O)_2NH_2$, —$S(O)_2$ $NHC_{1-4}$alkyl, —$S(O)_2N(C_{1-4}$alkyl$)_2$, $C_{1-6}$ alkylcarbonyl, $C_{1-6}$ alkoxycarbonyl, $CO_2H$, —S(O)R''', (where R''' is lower alkyl or cycloalkyl) and —$S(O)_2R''''$ (where R'''' is lower alkyl, cycloalkyl or OH).

In an embodiment $R_1$ or $R_1'$ is an optionally substituted pyrimidine.

In an embodiment $R_2$ is hydrogen.

In an embodiment $R_2$ is hydrogen, and $R_1$ or $R_1'$ is an optionally substituted pyridine or optionally substituted pyrimidine.

In an embodiment $R_3$ is optionally substituted $C_1$-$C_6$ alkyl

In an embodiment $R_3$ is $C_1$-$C_6$ alkyl.

In an embodiment $R_2$ is hydrogen, $R_1$ or $R_1'$ is an optionally substituted pyrimidine and $R_3$ is $C_1$-$C_6$ alkyl.

In an embodiment $R_4$ is selected from the group consisting of Cl, F, $C_{1-6}$ alkyl, $C_{1-6}$ alkoxy, halo $C_{1-6}$ alkyl (in particular —$CF_3$), halo $C_{1-6}$ alkoxy (in particular —$OCF_3$), optionally substituted phenyl, optionally substituted benzyl, optionally substituted phenoxy, optionally substituted benzyloxy, heterocyclyl, —$S(O)_2NH_2$, or —$S(O)_2NHC_{1-4}$alkyl, or —$S(O)_2N(C_{1-4}$alkyl$)_2$.

In an embodiment $R_2$ is hydrogen, $R_3$ is $C_1$-$C_4$ alkyl, for instance, methyl, ethyl, propyl, isopropyl, or butyl.

In an embodiment $R_1$ or $R_1'$ is selected from:

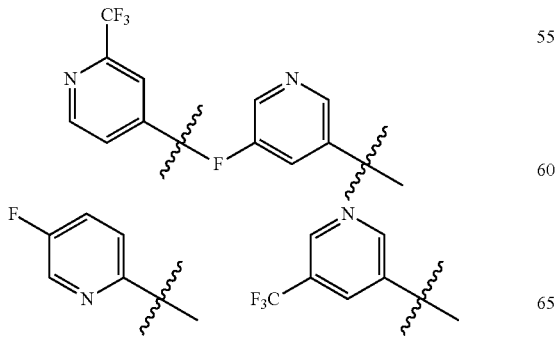

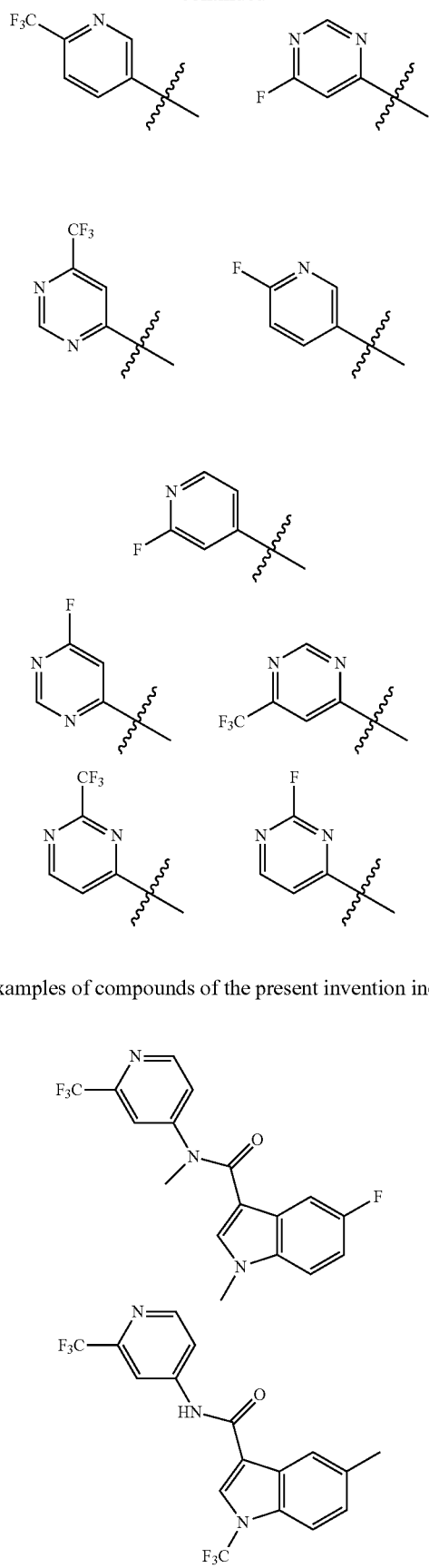

Examples of compounds of the present invention include:

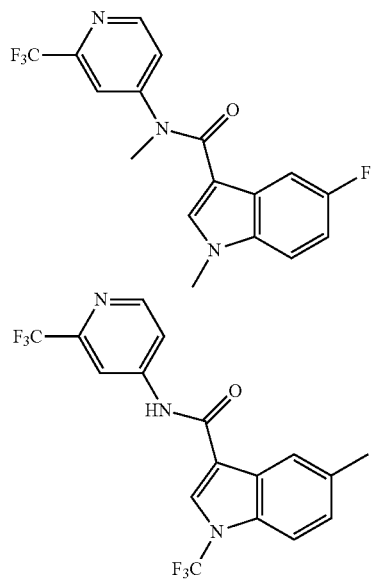

-continued

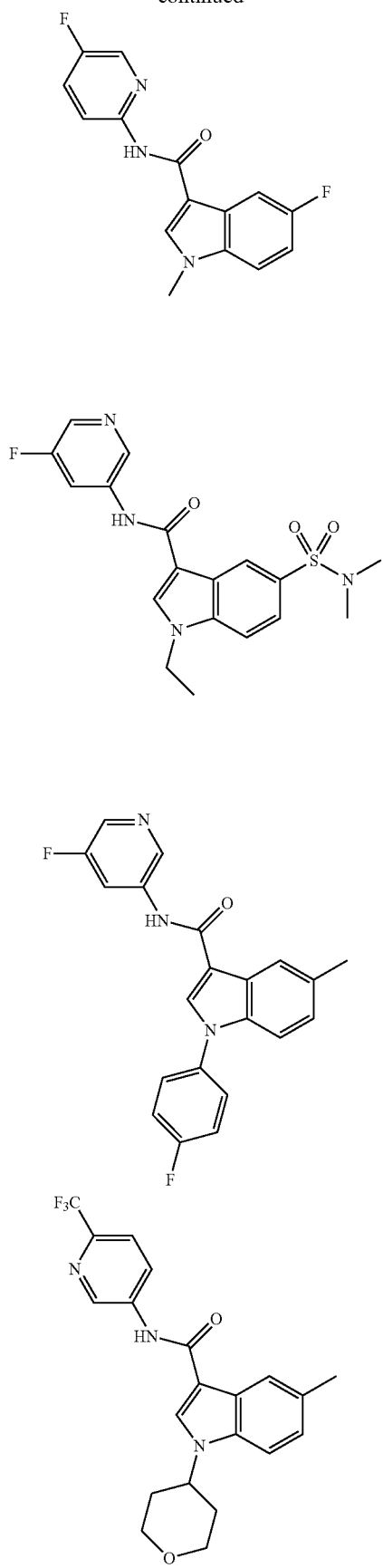

-continued

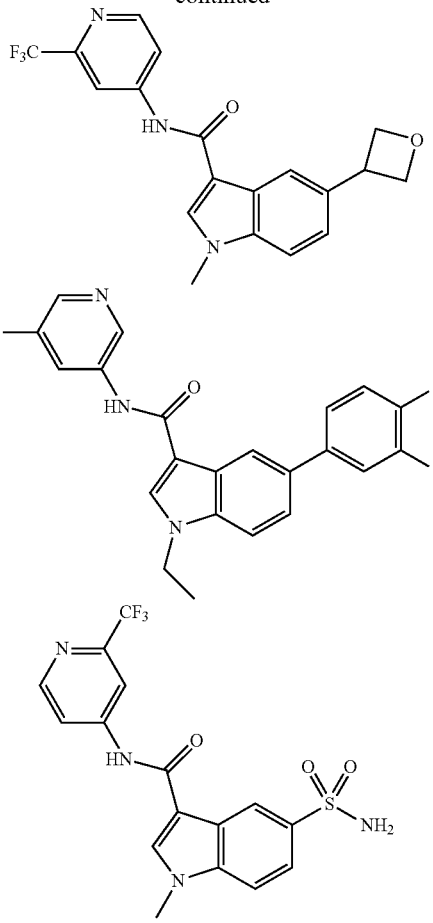

The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of the invention, or salts thereof. Pharmaceutically acceptable derivatives may include any pharmaceutically acceptable hydrate or any other compound or prodrug which, upon administration to a subject, is capable of providing (directly or indirectly) a compound of the invention, or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate.

The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of a salt thereof.

It will be appreciated that the compounds of the invention have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use as a positive allosteric modulator of α7nAChRs, more particularly as an anti-inflammatory or neuroprotective agent, the composition comprising an effective amount of a compound of the invention, or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy. For example the pharmaceutical preparation of the active compound may be co-administered (for example, separately, concurrently or sequentially), with one or more other agents used to treat cognitive impairment or mood disorders such as acetylcholine esterase inhibitors, antipsychotics, and antidepressants.

It is believed that the compounds of the invention may be beneficial in treating patients with cognition impairment or aid in increasing cognition. It is believed that this effect may be brought about by positive allosteric modulation of α7 nAChRs.

It is envisaged that the compounds may additionally be useful in the treatment of patients, including a mammal and especially a human, suffering from neuropsychiatric diseases and neurodegenerative diseases involving a dysfunction of the cholinergic system, and further conditions of memory and/or cognitive impairment, including, for example, schizophrenia, Attention Deficit Hyperactivity Disorder, anxiety, mania, depression, manic depression (as examples of neuropsychiatric disorders), Tourette's syndrome, Parkinson's disease, Huntington's disease (as examples of neurodegenerative diseases), and/or cognitive disorders (such as Alzheimer's disease, Lewy Body Dementia, Amyotrophic Lateral Sclerosis, memory impairment, memory loss, cognition deficit).

Neurodegenerative disorders include, but are not limited to, treatment and/or prophylaxis of Alzheimer's diseases, Pick's disease, diffuse Lewy Body disease, progressive supranuclear palsy (or Steel-Richardson syndrome), multi-system degeneration (or Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia.

The invention provides methods of treating subjects suffering from memory impairment due to, for example, Alzheimer's disease, mild cognitive impairment due to aging, schizophrenia, Attention Deficit Hyperactivity Disorder, Parkinson's disease, multiple sclerosis, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases.

For certain of the abovementioned conditions it is clear that the compounds may be used prophylactically as well as for the alleviation of symptoms.

References herein to "treatment" or the like are to be understood to include such prophylactic treatment, as well as therapeutic treatments.

The compounds of the present invention as agents which modulate the α7 nAChR may be particularly useful in the therapeutic or prophylactic treatment of diseases such as schizophrenia, bi-polar disorder, anxiety, AD, ADHD, mild cognitive impairment, Parkinson's Disease, Huntington's disease, Tourette's syndrome, brain trauma, jetlag and nicotine addiction.

Accordingly in a further aspect of the invention, there is provided a means for ameliorating the cognitive deficits associated with neurodegenerative and neuropsychiatric diseases and also inflammatory diseases by the application of a positive allosteric modulators of α7 nAChRs selected from a compound of the invention, or salt thereof, including a pharmaceutically acceptable derivative thereof, or a composition comprising the compound of the invention, or salt thereof, or a pharmaceutically acceptable derivative thereof.

In another aspect of the invention a method is provided for preventing or treating cognitive deficits involving dysfunction of the cholinergic system including the step of administrating a compound of the invention, or salt thereof, or a composition comprising the compound or salt thereof.

In another preferred form of the invention there is provided a method for preventing or treating neurodegenerative or neuropsychiatric disorders including the step of administrating a compound of the invention, or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect of the present invention, there is provided the use of a compound of the invention, or salt thereof, in the preparation of a medicament for the treatment (therapeutic or prophylactic) of disease states in which modulation of α7 nAChRs would be beneficial.

In a further aspect of the invention there is provided a process for the production of the compounds of the invention, or salts thereof, including pharmaceutically acceptable derivatives thereof.

Compounds of the invention may be prepared according to the following general scheme:

Scheme A

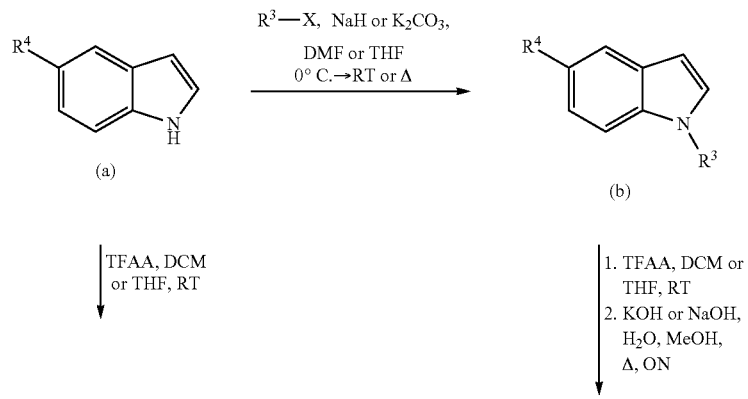

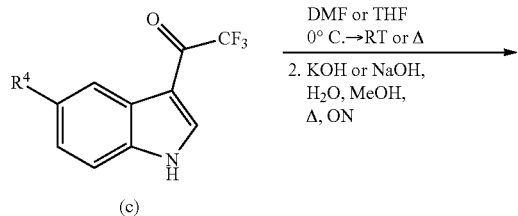

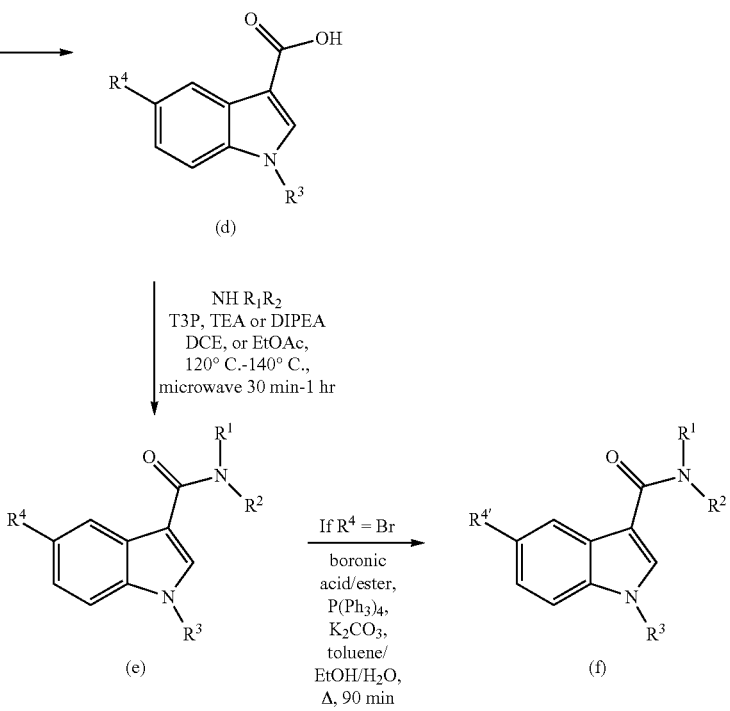

Compounds of Formula (I) can be prepared by synthetic procedures as depicted in Scheme A. Substituted indoles (a) are commercially available and may be N-alkylated using known procedures to give N-alkyl indole (b) or reacted with TFAA to give the 3-trifluoroethanone derivative (c). N-alkyl indole (b) may be converted to the 3-carboxylic acid (d) using TFAA followed by reaction with hydroxide. The 3-trifluoroethanone derivative (c) may be N-alkylated using known procedures and subsequently hydrolysed using known procedures to give the 3-carboxlic acid (d). Amide (e) can be generated by the coupling of carboxylic acid (d), with an amine using propylphosphonic anhydride (T3P) as the coupling agent to generate compounds of Formula (I) or (e). Numerous alternative amide formation procedures could be used such as the formation of acid chloride employing thionyl chloride or oxalyl chloride with catalytic DMF followed by reaction with amine or direct coupling of acid with amine in presence of dicyclohexyldiimide or other diimides or O-(7-azobenzotriazol-1-yl)-1,1,3,3-tetramethyl-uronium hexa fluorophosphate (HATU). Conversion of the carboxylic acid (d) to a mixed anhydride and reaction with amine is also feasible for the generation of compounds of Formula (I) or (e). If $R^4$=Br then amide (e) may be further functionalised through literature procedures such as a Suzuki coupling to give further analogues of Formula (I) or (f).

Another variation is to add, remove or modify the substituents of the product to form new derivatives. This could be achieved again by using standard techniques for functional group inter-conversion, well known in the industry such as those described in Comprehensive Organic Transformations: A Guide to Functional Group Preparations by Larock R C, New York, VCH Publishers, Inc. 1989.

Examples of possible functional group inter-conversions are: —C(O)NRR' from —$CO_2CH_3$ by heating with or without catalytic metal cyanide, e.g. NaCN, and HNRR' in $CH_3OH$; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R") SR'" with $H_3NR^+OAc^-$ by heating in alcohol; —C(NR'R") SR from —C(S)NR'R" with R—I in an inert solvent, e.g. acetone; —C(S)NR'R" (where R' or R" is not hydrogen) from —C(S)$NH_2$ with HNR'R"; —C(=NCN)—NR'R" from —C(=NR'R")—SR with $NH_2CN$ by heating in anhydrous alcohol, alternatively from —C(=NH)—NR'R" by treatment with BrCN and NaOEt in EtOH; —NR—C(=NCN)SR from —NHR' by treatment with $(RS)_2$C=NCN; —NR"$SO_2$R from —NHR' by treatment with $ClSO_2R$ by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —$NRSO_2CF_3$ from —NHR with triflic anhydride and base, —CH($NH_2$)CHO from —CH($NH_2$)C(O)OR' with Na(Hg) and HCl/EtOH; —$CH_2$C(O)OH from —C(O)OH by treatment with $SOCl_2$ then $CH_2N_2$ then $H_2O/Ag_2O$; —C(O)OH from —$CH_2$C(O)$OCH_3$ by treatment with PhMgX/HX then acetic anhydride then $CrO_3$; R—OC(O)R' from RC(O)R' by R"$CO_3H$; —CCH$_2$OH from —C(O)OR' with Na/R'OH; —CHCH$_2$ from —CH$_2$CH$_2$OH by the Chugaev reaction; —$NH_2$ from —C(O)OH by the Curtius reaction; —$NH_2$ from —C(O)NHOH with TsCl/base then $H_2O$; —CHC(O)CHR from —CHCHOHCHR by using the Dess-Martin Periodinane regent or $CrO_3$/aq$H_2SO_4$/acetone; —$C_6H_5$CHO from —$C_6H_5CH_3$ with $CrO_2Cl_2$; —CHO from —CN with $SnCl_2$/HCl; —CN from —C(O)NHR with $PCl_5$; —$CH_2$R from —C(O)R with $N_2H_4$/KOH; —S(O)$_2$R from —SR with mCPBA.

In order that the present invention may be more readily understood, we provide the following non-limiting examples.

EXAMPLES

Synthetic Procedure

Abbreviations
CDCl₃ d4-Chloroform
CD₃OD d4-Methanol
d6-DMSO d6-Dimethylsulfoxide
DCE Dichloroethane
DCM Dichloromethane
DIPEA Diisopropylethylamine
DMF Dimethylformamide
DMSO Dimethylsulfoxide
Et₂O Diethylether
EtOAc Ethyl Acetate
EtOH Ethanol
HATU O-(7-azobenzotriazol-1-yl)-1,1,3,3-tetramethyluronium hexa fluorophosphate
LCMS Liquid Chromatography Mass Spectrometry
LiAlH Lithium Aluminum Hydride
MgSO₄ Magnesium Sulphate
MeOH Methanol
NMR Nuclear Magnetic Resonance
TEA Triethylamine
TFAA Trifluoroacetic Anhydride
THF Tetrahydrofuran
pTLC Preparative Thin Layer Chromatography
T3P Propyl Phosphonic Anhydride All anhydrous solvents were commercially obtained and stored in Sure-Seal bottles under nitrogen. All other reagents and solvents were purchased as the highest grade available and used without further purification. Thin-layer chromatography (TLC) analysis of reaction mixtures was performed using Merck silica gel 60 F254 TLC plates and visualized using ultraviolet light. Silica gel 60 (40-63 μm, Merck) was used for flash chromatography. Melting points were measured using an Electrothermal 1002 apparatus and were uncorrected. ¹H NMR (300 MHz) and ¹³C NMR (75 MHz) spectra were obtained on a Bruker Advance 300 NMR spectrometer using residual signal of deuterated NMR solvent as internal reference. Mass spectral data and purity of all compounds were acquired on an Agilent LCMS-Ion Trap-1200 Series. Mass spectra were obtained on an Agilent Ion Trap applying electrospray ionization (ESI). Purity of all compounds was obtained using a Nucleodur 3 μm 4.6×150 mm reverse-phase column. The eluent was a linear gradient with a flow rate of 1.3 mL/min from 95% A and 5% B to 5% A and 95% B in 8.5 min (solvent A, H₂O with 0.1% HCO₂H; solvent B, acetonitrile with 0.1% HCO₂H). The compounds were detected at their maximum of absorbance.

In the examples below, in case the structures contain one or more stereogenic centres, the respective structure is depicted in an arbitrary absolute configuration. These structures depict single enantiomers as well as mixtures of enantiomers in all ratios, and/or mixtures of diastereoisomers in all ratios.

General Procedures

General Procedure A: Amide Bond Formation Using T3P

To a solution of the amine (1.0-1.2 eq.) and the carboxy-indole (1.0 eq.) in DCE or EtOAc (0.14-0.25 M) in a microwave vial, was added DIPEA or TEA (2.2-3.0 eq.) followed by T3P (50% in EtOAc) (2.4-3.0 eq.). The flask was sealed and heated to 120° C.-140° C. for 0.5-1 hr under microwave irradiation. Upon completion the reaction mixture was diluted with EtOAc and washed with NH₄Cl, Na₂CO₃ (sat. aq.) and brine. The organic phase was dried over MgSO₄ and concentrated in vacuo. The crude product was purified by silica gel column chromatography or pTLC to afford the desired amide.

General Procedure B: Alkylation of Indoles Using NaH

To a suspension of NaH (1.1-2.0 eq.) in DMF or THF (0.35-0.44 M) at 00° C. was added a solution of the indole (1.0 eq.) in DMF or THF followed by the halo-alkane (1.3-20 eq.). The reaction mixture was stirred for several minutes at 0° C. before warming to room temperature (or heating to 50° C. or reflux, to facilitate the reaction if required). Upon completion the reaction was quenched by addition of NH₄Cl and the product extracted into EtOAc (3×) or partitioned between EtOAc and HCl (1M), shaken, separated and extracted with EtOAc (2×), then washed with NH₄Cl. The combined extracts were washed with brine, dried over MgSO₄ and concentrated in vacuo.

General Procedure C: Formation of 3-Carboxy or 3-Trifluoroethanone Substituted Indoles with TFAA To the indole, either as a solution in DCM or THF at 0° C. or neat at room temperature, was added TFAA (1.5 eq.-3 eq.). The solution was stirred at room temperature until the 3-trifluoroethanone indole derivative had formed (approximately 10 min-1 hr).

If the desired material is the 3-trifluoroethanone derivative then the reaction was quenched by pouring onto water, collecting the resulting precipitate by vacuum filtration and washing the precipitate with water and ether before drying the crude material in vacuo for use without further purification.

If the desired material is the 3-carboxy derivative then the reaction mixture was concentrated in vacuo or the precipitate collected by vacuum filtration (as above) and the crude material taken up in KOH (20-40% aqueous) or NaOH (15% aqueous) with a small amount of MeOH added for solubility if required. The reaction mixture was heated to 80° C. overnight before cooling to room temperature and the MeOH (if used) removed in vacuo. The aqueous layer was acidified with HCl (2M) and the resulting precipitate collected by vacuum filtration for use without further purification.

Intermediate A 2,2,2-trifluoro-1-(5-fluoro-1H-indol-3-yl)ethanone

5-Fluoroindole (1.0 g, 7.4 mmol) was reacted as described under General Procedure C, isolating the desired 3-trifluoroethanone derivative, as a white solid (1.3 g, 76%). ESIMS m/z [M+H]⁺ 232.2.

Intermediate B 1-ethyl-5-fluoro-1H-indole-3-carboxylic acid

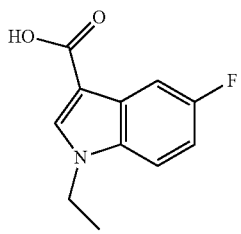

A suspension of Intermediate A (0.200 g, 0.866 mmol), potassium carbonate (0.299 g, 2.16 mmol) and iodoethane (104 μL, 1.3 mmol) in DMF (2.5 mL) was heated to 60° C., overnight in a sealed tube. The reaction mixture was cooled to room temperature, diluted with water (30 mL) and partitioned between the aqueous layer and EtOAc (70 mL). The organic phase was separated, dried (MgSO$_4$) and concentrated in vacuo. The resulting solid material was treated with KOH (20% aqueous, 10 mL) and heated to reflux overnight. The reaction mixture was cooled to room temperature and partitioned between water (50 mL) and EtOAc (100 mL). The biphasic solution was treated with HCl (1M, 25 mL) and vigorously shaken and separated. The organic phase was washed with brine, dried (MgSO$_4$) and concentrated in vacuo to yield the title compound as a pale yellow solid (120 mg, 67%) which was used without further purification. ESIMS m/z [M+H]$^+$ 208.2

Intermediate C 5-fluoro-1H-indole-3-carboxylic acid

5-Fluoroindole (0.505 g, 3.74 mmol) was reacted as described under General Procedure C to furnish the title compound (0.344, 51%) as a white/pale blue solid. ESIMS m/z [M–H]$^+$ 178.2.

Intermediate D 5-fluoro-1-methyl-1H-indole-3-carboxylic acid

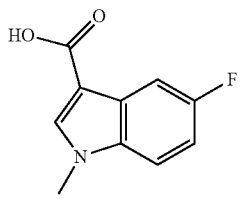

Intermediate C (0.934 g, 5.21 mmol) and methyl iodide (14.8 g, 0.104 mol) were reacted as described under General Procedure B to furnish the title compound (0.979 g, 97%) which was used without purification in the next step. ESIMS m/z [M+H]$^+$ 194.2.

Intermediate E 5-fluoro-1-(propan-2-yl)-1H-indole-3-carboxylic acid

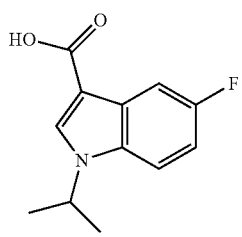 [SMILES: CC(C)n1cc(C(=O)O)c2cc(F)ccc21]

Intermediate A (0.210 g, 0.908 mmol) and 2-bromopropane (0.111 mL, 1.18 mmol) were reacted as described under General Procedure B to furnish the title compound (120 mg, 60%) as a pale yellow solid which was used without further purification. ESIMS m/z [M–H]$^+$ 222.2.

Intermediate F 5-methyl-1H-indole-3-carboxylic acid

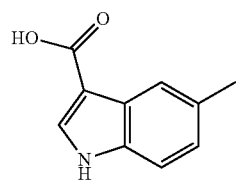

5-Methylindole (0.500 g, 3.81 mmol) was reacted as described under General Procedure C to furnish the title compound (0.448 g, 67%) as a cream solid. ESIMS m/z [M–H]$^+$ 176.2.

Intermediate G 1,5-dimethyl-1H-indole-3-carboxylic acid

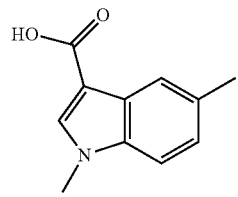

Intermediate F (0.373 g, 2.13 mmol) and methyl iodide (6.05 g, 42.6 mmol) were reacted as described under General Procedure B to furnish the title compound (0.275 g, 68%) as a beige solid which was used without further purification in the next step. ESIMS m/z [M−H]+ 190.2.

Intermediate H 1-methyl-5-(trifluoromethyl)-1H-indole

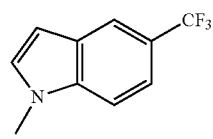

5-(Trifluoromethyl)indole (0.364 g, 1.43 mmol) and methyl iodide (0.912 g, 46.43 mmol) were reacted as described under General Procedure B to furnish the title compound which was used immediately without further purification in the next step.

Intermediate I 1-methyl-5-(trifluoromethyl)-1H-indole-3-carboxylic acid

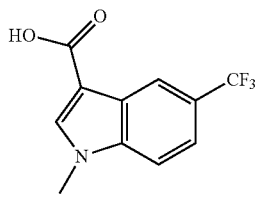 [SMILES: Cn1cc(C(=O)O)c2cc(C(F)(F)F)ccc21]

Intermediate H (0.285 g, 1.43 mmol) was reacted as described under General Procedure C to furnish the title compound (0.343 g, 99% over 2 steps) which was used without further purification in the next step. ESIMS m/z [M−H]+ 242.3.

Intermediate J 5-bromo-1-methyl-1H-indole

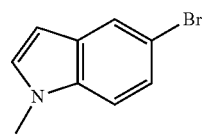

5-bromoindole (2.390 g, 12.19 mmol) and methyl iodide (7.068 g, 49.80 mmol) were reacted as described under General Procedure B to furnish the title compound (2.407, 94%) after purification by column chromatography (10-20% DCM/hexane). ESIMS m/z [M+H]+ 210.0.

Intermediate K 5-bromo-1-methyl-1H-indole-3-carboxylic acid

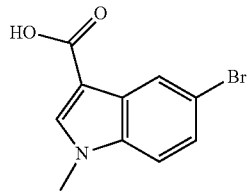

Intermediate J (1.109 g, 5.28 mmol) was reacted as described under General Procedure C to furnish the title compound (1.318 g, 98%) which was used without further purification in the next step. ESIMS m/z [M+H]+ 252.2.

Intermediate L 5-bromo-1-methyl-N-[2-(trifluoromethyl)pyridin-4-yl]-1H-indole-3-carboxamide

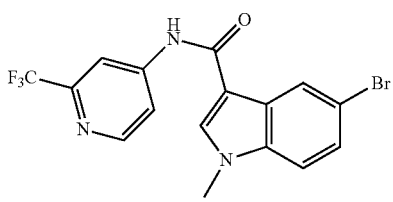 [SMILES: Cn1cc(C(=O)Nc2ccnc(C(F)(F)F)c2)c2cc(Br)ccc21]

Intermediate K (0.485 g, 1.908 mmol) and 4-amino-2-(trifluoromethyl)pyridine (0.379 g, 2.336 mmol) were reacted as described under General Procedure A to furnish the title compound (327 mg, 43%) after purification by column chromatography, twice (50-80% EtOAc/hexane and 0-20% EtOAc/DCM). ESIMS m/z [M+H]+ 399.0.

Intermediate M 1-(2-ethoxy-2-oxoethyl)-5-fluoro-1H-indole-3-carboxylic acid

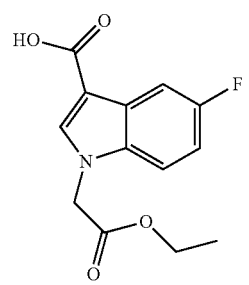 [SMILES: CCOC(=O)Cn1cc(C(=O)O)c2cc(F)ccc21]

Intermediate C (101 mg, 0.561 mmol) and ethyl bromoacetate (70 μL, 0.631 mmol) were reacted as described under General Procedure B to furnish the title compound (70 mg, 47%) after purification by column chromatography (20-30% EtOAc/DCM). ESIMS m/z [M−H]+ 264.2.

25

Intermediate N ethyl (5-fluoro-3-{[2-(trifluoromethyl)pyridin-4-yl]carbamoyl}-1H-indol-1-yl)acetate

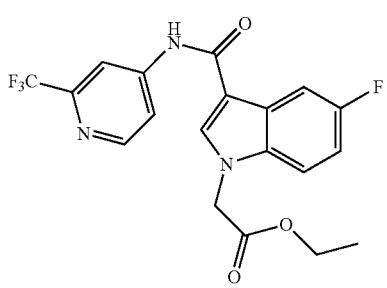 [SMILES: CCOC(=O)Cn1cc(C(=O)Nc2ccnc(C(F)(F)F)c2)c2cc(F)ccc21]

To a solution of Intermediate M (67 mg, 0.254 mmol) in DCM (3 mL) and DMF (10 µL) was added oxalyl chloride (65 µL, 0.768 mmol). The solution was stirred at room temperature for 4 hours before concentrating in vacuo. The crude residue was taken up in 1,2-DCE (3 mL) and added to a solution of 4-amino-2-(trifluoromethyl)pyridine (51 mg, 0.316 mmol) in pyridine (0.5 mL). The reaction was irradiated in the microwave for 1 hr. at 110 OC before quenching with NH$_4$Cl (sat. aq.) and extracting into EtOAc (3×). The combined extracts were dried (MgSO$_4$) and concentrated in vacuo. The crude material was purified by column chromatography (10-20% EtOAc/DCM) to furnish the title compound (83 mg, 80%). ESIMS m/z [M+H]$^+$ 410.0.

Example 1

1-ethyl-5-fluoro-N-(5-fluoropyridin-3-yl)-1H-indole-3-carboxamide

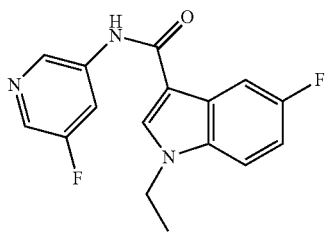 [SMILES: CCn1cc(C(=O)Nc2cncc(F)c2)c2cc(F)ccc21]

Intermediate B (60 mg, 0.29 mmol) and 3-amino-5-fluoro-pyridine (39 mg, 0.35 mmol) were reacted as described under General Procedure A to furnish the title compound (23 mg, 26%) as a white solid after purification by pTLC (100% DCM). $^1$H NMR (300 MHz, CDCl$_3$) δ 8.38 (brs, 1H), 8.34-8.29 (m, 1H), 8.23-8.22 (m, 1H), 7.82 (s, 1H), 7.81-7.77 (m, 1H), 7.66 (brs, 1H), 7.37-7.33 (m, 1H), 7.12-7.06 (m, 1H), 4.27-4.20 (m, 2H), 1.59-1.53 (m, 3H). ESIMS m/z [M+H]$^+$ 302.3.

26

Example 2

1-ethyl-5-fluoro-N-[6-(trifluoromethyl)pyrimidin-4-yl]-1H-indole-3-carboxamide

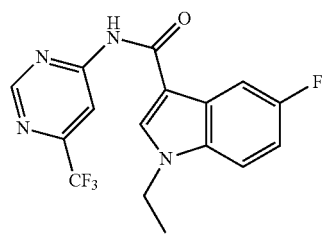 [SMILES: CCn1cc(C(=O)Nc2cc(C(F)(F)F)ncn2)c2cc(F)ccc21]

Intermediate B (140 mg, 0.676 mmol) and 6-trifluoromethyl-4pyrimidinamine (122 mg, 0.748 mmol) were reacted as described under General Procedure A to furnish the title compound (89 mg, 43%) as a white solid after purification by pTLC (100% DCM). $^1$H NMR (300 MHz, CDCl$_3$) δ 8.97 (s, 1H), 8.71 (s, 1H), 8.46 (brs, 1H), 7.92-7.88 (m, 1H), 7.84 (s, 1H), 7.38-7.34 (m, 1H), 7.14-7.07 (m, 1H), 4.29-4.21 (m, 2H), 1.60-1.55 (m, 3H). ESIMS m/z [M+H]$^+$ 353.2.

Example 3

1-ethyl-5-fluoro-N-[6-(trifluoromethyl)pyridin-3-yl]-1H-indole-3-carboxamide

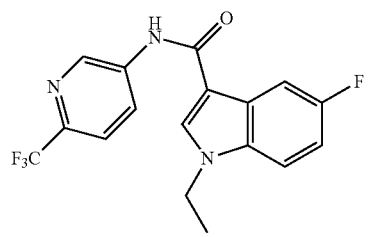 [SMILES: CCn1cc(C(=O)Nc2ccc(C(F)(F)F)nc2)c2cc(F)ccc21]

Intermediate B (54 mg, 0.26 mmol) and 3-amino-6-(trifluoromethyl)pyridine (46 mg, 0.29 mmol) were reacted as described under General Procedure A to furnish the title compound (33 mg, 36%) after purification twice by pTLC (10% EtOAc/CHCl$_3$ and 60% EtOAc/hexane) followed by purification twice by silica gel column chromatography (50% EtOAc/hexane and 50-100% Et$_2$O/hexane). $^1$H NMR (300 MHz, d$_6$-DMSO) δ 10.4 (s, 1H), 9.10-9.09 (m, 1H), 8.55-8.52 (m, 2H), 7.95-7.90 (m, 2H), 7.73-7.68 (m, 1H), 7.22-7.15 (m, 1H), 4.40-4.33 (m, 2H), 1.53-1.48 (m, 3H). ESIMS m/z [M+H]$^+$ 352.7.

Example 4

1-ethyl-5-fluoro-N-[2-(trifluoromethyl)pyrimidin-4-yl]-1H-indole-3-carboxamide

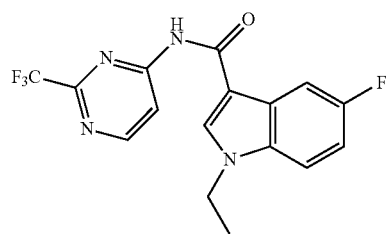 [SMILES: CCn1cc(C(=O)Nc2ccnc(C(F)(F)F)n2)c2cc(F)ccc21]

Intermediate B (53 mg, 0.25 mmol) and 2-trifluoromethyl-4-pyrimidinamine (46 mg, 0.28 mmol) were reacted as described under General Procedure A to furnish the title compound (27 mg, 30%) after purification by pTLC (20-30% EtOAc/hexane). $^1$H NMR (300 MHz, CDCl$_3$) δ 8.77-8.75 (m, 1H), 8.52-8.50 (m, 1H), 8.39 (brs, 1H), 7.96-7.92 (m, 1H), 7.86 (s, 1H), 7.38-7.33 (m, 1H), 7.14-7.07 (m, 1H), 4.29-4.22 (m, 2H), 1.60-1.55 (m, 3H). ESIMS m/z [M+H]$^+$ 353.0.

Example 5

5-fluoro-1-methyl-N-[2-(trifluoromethyl)pyridin-4-yl]-1H-indole-3-carboxamide

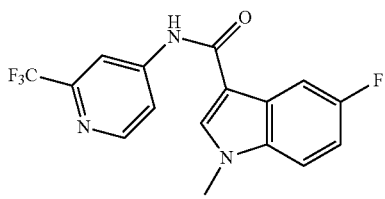 [SMILES: Cn1cc(C(=O)Nc2ccnc(C(F)(F)F)c2)c2cc(F)ccc21]

Intermediate D (0.300 g, 1.55 mmol) and 4-amino-2-(trifluoromethyl)pyridine (0.504 g, 3.11 mmol) were reacted as described under General Procedure A to furnish the title compound (39 mg, 8%) following purification by column chromatography (40-100% EtOAc/CHCl$_3$), followed by recrystallisation from EtOAc/Hexane and then a final pTLC purification (50% EtOAc/hexane). $^1$H NMR (300 MHz, CDCl$_3$) δ 8.64-8.61 (m, 1H), 8.00-7.99 (m, 1H), 7.82-7.77 (m, 3H), 7.73 (brs, 1H), 7.36-7.32 (m, 1H), 7.15-7.08 (m, 1H), 3.89 (s, 3H). ESIMS m/z [M+H]$^+$ 338.3.

Example 6

5-fluoro-N-(5-fluoropyridin-3-yl)-1-(propan-2-yl)-1H-indole-3-carboxamide

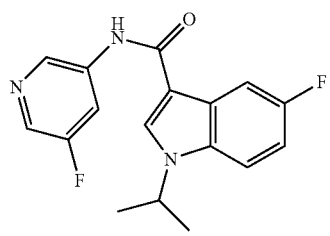 [SMILES: CC(C)n1cc(C(=O)Nc2cncc(F)c2)c2cc(F)ccc21]

Intermediate E (70 mg, 0.338 mmol) and 3-amino-5-fluoropyridine (44 mg, 0.393 mmol) were reacted as described under General Procedure A to furnish the title compound (19 mg, 19%) as a pale yellow solid after purification by pTLC (10% EtOAc/DCM). $^1$H NMR (300 MHz, CDCl$_3$) δ 8.39 (brs, 1H), 8.34-8.29 (m, 1H), 8.23-8.22 (m, 1H), 7.91 (s, 1H), 7.80-7.76 (m, 1H), 7.68 (brs, 1H), 7.41-7.36 (m, 1H), 7.12-7.05 (m, 1H), 4.77-4.65 (m, 1H), 1.61-1.58 (m, 6H). ESIMS m/z[M+H]$^+$ 316.3.

Example 7

1,5-dimethyl-N-[2-(trifluoromethyl)pyridin-4-yl]-1H-indole-3-carboxamide

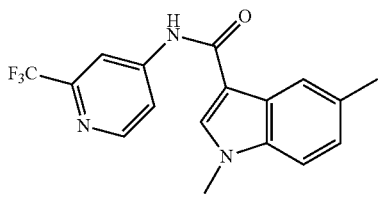 [SMILES: Cc1ccc2c(c1)c(C(=O)Nc1ccnc(C(F)(F)F)c1)cn2C]

Intermediate G (71 mg, 0.375 mmol) and 4-amino-2-(trifluoromethyl)pyridine (122 mg, 0.750 mmol) were reacted as described under General Procedure A to furnish the title compound (5 mg, 4%) after purification by pTLC, twice (40% EtOAc/CHCl$_3$). $^1$H NMR (300 MHz, CDCl$_3$) δ 8.63-8.61 (m, 1H), 8.02-8.01 (m, 1H), 7.84-7.80 (m, 3H), 7.73 (s, 1H), 7.33-7.30 (m, 1H), 7.21-7.18 (m, 1H), 3.86 (s, 3H), 2.54 (s, 3H). ESIMS m/z [M+H]$^+$ 334.2.

Example 8

1,5-dimethyl-N-[6-(trifluoromethyl)pyrimidin-4-yl]-1H-indole-3-carboxamide

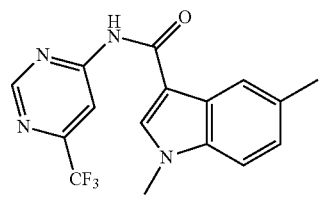 [SMILES: Cc1ccc2c(c1)c(C(=O)Nc1cc(C(F)(F)F)ncn1)cn2C]

Intermediate G (52 mg, 0.276 mmol) and 6-trifluoromethyl-4-pyrimidinamine (45 mg, 0.276 mmol) were reacted as described under General Procedure A to furnish the title compound (30 mg, 33%) as a white solid after purification by column chromatography (10% EtOAc/DCM). $^1$H NMR (300 MHz, CDCl$_3$) δ 8.98 (s, 1H), 8.75 (s, 1H), 8.52 (brs, 1H), 7.96 (s, 1H), 7.76 (s, 1H), 7.33-7.30 (m, 1H), 7.22-7.19 (m, 1H), 3.88 (s, 3H), 2.54 (s, 3H). ESIMS m/z [M+H]$^+$ 335.0.

Example 9

1-methyl-5-(trifluoromethyl)-N-[2-(trifluoromethyl)pyridin-4-yl]-1H-indole-3-carboxamide

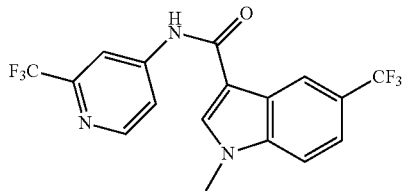 [SMILES: Cn1cc(C(=O)Nc2ccnc(C(F)(F)F)c2)c2cc(C(F)(F)F)ccc21]

Intermediate I (62 mg, 0.254 mmol) and 4-amino-2-(trifluoromethyl)pyridine (45 mg, 0.276 mmol) were reacted as described under General Procedure A to furnish the title compound (12.3 mg, 13%) after purification by column chromatography (0-15% EtOAc/DCM) and four pTLC's (100% DCM->15% Et$_2$O/DCM, 10% Et$_2$O/DCM (twice), 60% EtOAc/hexane). $^1$H NMR (300 MHz, CD$_3$OD) δ 8.61-8.60 (m, 1H), 8.57-8.55 (m, 1H), 8.27-8.26 (m, 2H), 8.03-8.00 (m, 1H), 7.69-7.66 (m, 1H), 7.59-7.55 (m, 1H), 3.98 (s, 3H). ESIMS m/z [M+H]$^+$ 388.0.

Example 10

N-(5-fluoropyridin-3-yl)-1-methyl-5-(trifluoromethyl)-1H-indole-3-carboxamide

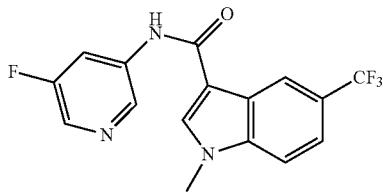 [SMILES: Cn1cc(C(=O)Nc2cncc(F)c2)c2cc(C(F)(F)F)ccc21]

Intermediate I (68 mg, 0.280 mmol) and 3-amino-5-fluoropyridine (36 mg, 0.320 mmol) were reacted as described under General Procedure A to furnish the title compound (12.3 mg, 13%) after purification by column chromatography (100% EtOAc). $^1$H NMR (300 MHz, CD$_3$OD) δ 8.66 (brs, 1H), 8.60-8.58 (m, 1H), 8.30-8.52 (m, 1H), 8.22 (s, 1H), 8.19-8.18 (m, 1H), 7.68-7.65 (m, 1H), 7.58-7.54 (m, H), 3.97 (s, 3H). ESIMS m/z [M+H]$^+$ 338.3.

Example 11

1-methyl-5-(1-methyl-1H-pyrazol-4-yl)-N-[2-(trifluoromethyl)pyridin-4-yl]-1H-indole-3-carboxamide

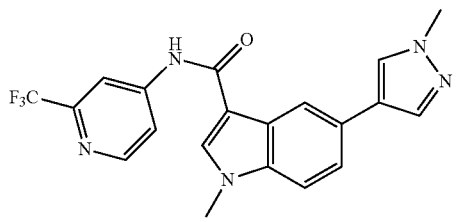 [SMILES: Cn1cc(-c2ccc3c(c2)c(C(=O)Nc2ccnc(C(F)(F)F)c2)cn3C)cn1]

To a solution of Intermediate L (55 mg, 0.138 mmol) and Pd(PPh$_3$)$_4$ (9.3 mg, 0.008 mmol) in toluene (4 mL) was added 1-methylpyrazole-4-boronic acid pinacol ester (114 mg, 0.548 mmol) as a solution in EtOH (2 mL). A solution of K$_2$CO$_3$ (116 mg, 0.836 mmol) in H$_2$O was added and the reaction mixture heated to 100° C. for 90 minutes. The reaction mixture was cooled to room temperature and partitioned between H$_2$O (10 mL) and EtOAc (20 mL) and the layers separated. The aqueous phase was again extracted with EtOAc (10 mL) and the combined extracts dried (MgSO$_4$) and concentrated in vacuo. The product was purified by column chromatography (50-90% EtOAc/DCM) and then pTLC (50% EtOAc/DCM) to yield the desired product (54 mg, 98%). $^1$H NMR (300 MHz, d$_6$-DMSO) δ 10.4 (s, 1H), 8.63-8.61 (m, 1H), 8.37-8.32 (m, 3H), 8.15 (s, 1H), 7.99-7.97 (m, 1H), 7.83 (s, 1H), 7.59-7.50 (m, 2H), 3.91 (s, 3H), 3.88 (s, 3H). ESIMS m/z [M+H]$^+$ 400.0.

Example 12

5-fluoro-1-(2-hydroxyethyl)-N-[2-(trifluoromethyl)pyridin-4-yl]-1H-indole-3-carboxamide

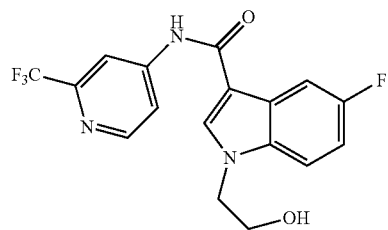 [SMILES: O=C(Nc1ccnc(C(F)(F)F)c1)c1cn(CCO)c2ccc(F)cc12]

To a solution of Intermediate N (80 mg, 0.195 mmol) in anhydrous THF (3 mL) at 0° C. was added LiAlH$_4$ (20 mg, 0.519 mmol) and the reaction mixture was allowed to warm to room temperature over 30 minutes. The reaction mixture was diluted with EtOAc and quenched by careful addition of sodium potassium tartrate (1M aq.). The layers were separated and the aqueous further extracted with EtOAc (2×). The combined extracts were dried (MgSO$_4$) and concentrated in vacuo. The product was purified by column chromatography (50-100% EtOAc/DCM) to yield the desired product (44 mg, 61%). $^1$H NMR (300 MHz, d$_6$-DMSO) δ 10.5 (s, 1H), 8.63-8.61 (m, 1H), 8.49 (s, 1H), 8.31-8.30 (m, 1H), 8.04-8.01 (m, 1H), 7.93-7.88 (m, 1H), 7.69-6.64 (m, 1H), 7.17-7.10 (m, 1H), 5.09-5.05 (m, 1H), 4.35-4.31 (m, 2H), 3.80-3.75 (m, 2H). ESIMS m/z [M+H]$^+$ 368.0.

Pharmacology

Example P1

CellLux Fluorescence Assay to Detect Aconists and Positive Allosteric Modulators of α7 nAChR Compounds were screened for positive allosteric modulation (PAM) of α7 nACh receptors on the CellLux (Perkin Elmer) with a fluorescence-based calcium assay. Activation of the α7 nAChR by endogenous ligands, results in a calcium flux which can be measured using ion specific fluorescent dyes. The fluorescence assay was run in a high throughput format on the CellLux, an automated fluorescent plate reader with liquid handling capabilities. The assay measured intracellular calcium changes in a GH4C$_1$ cell line stably expressing α7 nAChRs, when treated with compounds that positively modulated an ACh-induced response. Compound was added first to identify any agonist activity followed by ACh addition (EC20 concentration) to measure PAM activity.

Prior to assay, α7/GH4C$_1$ cells were seeded in 96-well plates (PDL-coated) and incubated for 48 hours at 33° C. in 5% CO$_2$. The cells were grown in F10OHam media plus 15% horse serum, 2.5% FCS, 2 mM penicillin, 2 mM streptomycin, 2 mM glutamine and 10 mM Hepes (Invitrogen). 0.5 mM sodium butyrate, a growth arrestor, was added to the cells during the incubation period to increase expression of α7 nAChR. On the day of assessment, the media was removed and the cells were washed with HBSS buffer (1 mM CaCl$_2$, 0.5 mM MgCl$_2$, 0.4 mM MgSO$_4$, 5 mM KCL, 0.4 mM KHPO$_4$, 4 mM NaHCO$_3$, 137 mM NaCl, 0.3 mM Na$_2$HPO$_4$, 5.5 mM glucose and 1M Hepes, pH7.4) and then Fluo-4 Direct Calcium dye (Molecular Probes; Excitation: 495 nm; Emission: 516 nm) was added. The cells were incubated with dye for 30 minutes at 33° C. Compound addition, ACh addition and fluorescence measurements were performed on the CellLux.

The CellLux recorded fluorescent responses at 5 second intervals starting with a 10 second baseline reading, the compound was then added and the response was read for 1 minute. ACh was then added and the response read for a further 2 minutes, a total of 4 minutes. This protocol detects agonist and PAM activity of compounds at the α7 nAChR.

Compounds were tested at 6 doses, in triplicate, 0.03, 0.1, 0.3, 1, 3 and 10 uM. Working stocks were prepared in DMSO from 10 mM DMSO stocks and then 10× starting stocks were prepared by diluting 1:100 in HBSS buffer (0.1% DMSO final). A 10× starting dilution of an EC20 concentration of ACh was prepared in HBSS buffer (0.1% DMSO final). Negative control was HBSS buffer (0.1% DMSO final).

Data was analysed by calculating % potentiation of compound compared to the ACh control response, where ACh potentiation was set at 0%. Peak/base values were calculated for each compound concentration (n=3) using AssayPro program (CellLux) and these values were used to determine % potentiation based on the ACh control peak/base value. Compounds were identified as active if they showed statistically significant potentiation of the control ACh response. For active compounds % potentiation values were used to calculate compound EC50 values in GraphPad Prism 4.

Example P2

Electrophysiololqy Protocol to Detect α7 nAChR Positive Allosteric Modulator Activity Compound Preparation:
Tested compounds were prepared by serial dilutions of 10 mM stock solution in DMSO to concentrations of the compound 1000 times higher than its final concentration. The DMSO stock solutions were then diluted 1:100 in the recording buffer bringing DMSO concentration to 1%. These intermediate solutions were further diluted 10 times with buffer to obtain final concentrations and lower DMSO concentration to 0.1%.

Acetylcholine chloride (ACh) purchased from Sigma-Aldrich (Sigma-Aldrich, St Louis, Mo.) was used as an α7 nAChR agonist at a concentration corresponding to EC$_{20}$ measured by peak current.

Calculation of the Effect on α7 nAChR-Mediated Currents:
The effect of tested compounds on ACh-evoked currents was calculated by the following formula:

$$\text{Effect}(\%) = \left(\left(\frac{I_{compound}}{I_{control}}\right) - 1\right) \times 100$$

Therefore, zero indicates no effect, negative numbers correspond to percentage of inhibition and positive numbers to percentage of potentiation relative to control ACh responses at EC$_{20}$.

The formula was used for calculations of effects on both peak current and area under curve (AUC).

Example P2.1

Automated Planar Patch-Clamp:

Compounds of the invention may be evaluated by electrophysiology using a Patchliner® (Nanion Technologies GmbH, Germany), an automated planar patch-clamp platform of medium throughput was used as a first step in electrophysiological assessment of α7 nAChR positive allosteric modulators (PAMs).

Briefly, intracellular (KCl—50 mM, NaCl—10 mM, KF—60 mM, EGTA—20 mM, HEPES—10 mM, pH—7.2, 285 mOsmol) and extracellular (NaCl—140 mM, KCl—4 mM, CaCl$_2$-2 mM, MgCl$_2$—1 mM, HEPES—10 mM, D-Glucose—5 mM, pH—7.4, 298 mOsmol) solutions were automatically pipetted onto NPC-16 chip (medium resistance ~2.5-2.6 MΩ). Suspension of GH4C$_1$ cells expressing rat α7 nAChRs was introduced in 4 wells of a medium resistance chip and suction was applied to attract cells in the holes. The extracellular solution was subsequently exchanged to high calcium solution (NaCl—80 mM, KCl—3 mM, CaCl$_2$—45 mM, HEPES—10 mM, pH—7.4, 298 mOsmol) followed by gigaohm seal formation and obtaining whole-cell configuration. The rest of protocol was carried out in the high-calcium recording solution. Holding potential was −70 mV throughout the protocol. A control response to 60 or 100 μM of ACh was obtained first. Next, a cell was pre-incubated with compound of interest at 3 μM for ~30 s after which the compound was co-applied with acetylcholine.

Amplitude of the responses was measured in HEKA Patchmaster software (HEKA Elektronik, Germany) and percentage of potentiation calculated. Recording was repeated unless a minimum of two replicates had been obtained per compound.

Example P2.2

Manual Patch Clamp:

Compound of the invention may be evaluated by electrophysiology on a manual patch-clamp setup using a fast-application add-on Dynaflow® (Cellectricon AB, Sweden). The fast application system allows resolution of true peak amplitudes, which otherwise would be affected by rapid receptor desensitization, and thus greatly improves measurement precision with fast ligand gated channels such as α7 nAChR.

GH4C$_1$ cells expressing rat α7 nAChRs were patch-clamped in the recording chamber of 16-channel re-usable Dynaflow® ReSolve chips using EPC$_{10}$ USB amplifier (HEKA Elektronik, Germany). Extracellular solution contained NaCl—137 mM, KCl—5 mM, CaCl$_2$—2.5 mM, MgCl$_2$—1 mM, HEPES—10 mM, D-Glucose—10 mM, pH—7.4. Thin wall borosilicate glass electrodes (Harvard Apparatus) were pulled to a resistance of 2-4 MΩ when filled with intracellular solution (K$^+$-gluconate—120 mM, KCl—5 mM, HEPES—10 mM, EGTA—10 mM, MgCl$_2$—1 mM, ATP—2 mM, pH—7.2). Cells were held at −70 mV. Cells with series resistance below 15 MΩ were kept and 40% compensation was utilized routinely.

The recording protocol consisted of obtaining of two control ACh responses (EC$_{20}$, peak, 250 ms pulse) prior to 30 s pre-incubation with a tested compound (3 μM) followed by 250 ms co-application of 3 μM compound plus EC$_{20}$ ACh. Dose-responses for selected compounds were obtained by a continuous compound application of increasing concentrations alternated with co-applications of compound plus $EC_{20}$ ACh every 30 seconds.

Current amplitudes along with net charge carried (area under curve, AUC) were measured in Patchmaster software (HEKA Elektronik, Germany) and percentage of peak current and AUC potentiation by test compounds was calculated using the above mentioned formula. Dose-responses for selected compounds were fitted and plotted in Prism4/5 (GraphPad Software, Inc., CA).

Example P3:

Animal Model of Cognitive Enhancement—T-Maze Continuous Alternation Task (T-CAT)

The cognition enhancing properties of the compounds in the invention were evaluated in an animal model where cognitive impairment is pharmacologically induced by Scopolamine, a muscarinic receptor antagonist which is used as a standard/reference drug for inducing cognitive deficits in healthy humans and animals.

The T-maze Continuous Alternation Task (T-CAT) measures spontaneous alternation, which is the innate tendency of mice to alternate free choices in a T-maze over a series of successive runs. This sequential procedure relies on working memory and is sensitive to various pharmacological manipulations affecting memory processes.

The T-maze apparatus is made of gray Plexiglas with a main stem (55 cm long×10 cm wide×25 cm high) and two arms (30 cm long×10 cm wide×25 cm high) positioned at 90 degree angle relative to the main stem. A start box (15 cm long×10 cm wide) is separated from the main stem by a sliding door. Sliding doors are also provided to close specific arms during the forced-choice alternation task.

The experimental protocol consists of one single session, which starts with 1 "forced-choice" trial, followed by 14 "free-choice" trials. In the first "forced-choice" trial, the animal is confined for 5 s in the start arm and then it is released while either the left or right goal arm is blocked by a sliding door. The animal will negotiate the maze, eventually enter the open goal arm, and return to the start position. Immediately after the return to the start position, the left or right goal door is opened and the animal is allowed to choose freely between the left and right goal arm ("free choice" trials). The animal is considered to have entered an arm when it places four paws in the arm. A session is terminated and the animal is removed from the maze as soon as 14 free-choice trials have been performed or 10 minutes have elapsed, whichever event occurs first. The percentage of alternation over the 14 free-choice trials is determined for each mouse and is used as an index of working memory performance. This percentage is defined as entry in a different arm of the T-maze over successive visits (i.e., left-right-left-right, etc).

Scopolamine administered 20 minutes prior the initiation of the T-maze session is used to induce disruption in the spontaneous alternation of mice. Test compounds are administered 60 minutes prior the start of the T-maze session in order to evaluate their ability to reverse the scopolamine effect.

The apparatus is cleaned between each animal using alcohol (70°). Urine and faeces are removed from the maze. During the trials, animal handling and the visibility of the operator are minimized as much as possible.

Example P4:

Animal Model of Cognitive Enhancement—Novel Object Recognition Test—Rat

The object recognition task is used to assess the short term memory in rats and is based on the natural tendency of rats to preferentially explore a novel versus a familiar object, which requires memory of the familiar object.

Equipment

The apparatus consists of an open acrylic glass cage (101 cm×101 cm; with 45 cm walls) within which animals can move freely. The two objects used in the assay are a metallic ball and a black box. The animal's approaches to the objects are recorded by an observer using stopwatch.

Methods

Step 1—Habituation:

Twenty four hours before the first trial, animals are allowed to habituate to the open-field apparatus for 15 minutes.

Step 2—Acquisition Trial:

One object (Object A) is placed in a particular corner of the central square. Animals are randomly exposed to the experimental situation for 10 minutes. Their explorative approaches to the object are recorded. Animals which don't display locomotor activity (total immobility) or do not explore the object are excluded.

Step 3—Retention Trial:

The test for retention is performed 30 minutes after the acquisition trial. Object A and the second object (Object B) are placed on adjacent corners of the central square. Each animal is exposed to the experimental situation for 10 minutes while exploratory approaches towards the two objects are recorded.

Step 4—Recognition Index:

For each animal, the time taken to explore object A (tA) and object B (tB) are recorded and the recognition index (RI) determined using the formula: $RI=tB/(tA+tB)\times 100$ where tB is the time spent exploring Object B and tA is the time spent exploring object A, values which are collected during the retention trial. In addition, the results are also expressed as the difference between exploration time of the new and the familiar objects.

Drugs and Treatment Groups:

Each animal receives test substances or vehicle treatments at times shown below:

| Groups | Treatment | Time |
| --- | --- | --- |
| Control | vehicle (per os) | 1 hour before the acquisition trial |
| Scopolamine | 0.6 mg/kg (i.p.) | 20 min before the acquisition trial |
| Test Compounds | (dose) mg/kg (per os) | 1 hour before the acquisition trial |

Data Analysis

One-way analysis of variance (ANOVA) followed by Fisher's Protected Least Significant Difference is used to compare pairs of group means. $p \leq 0.05$ are deemed significant.

Biological Data

Compounds shown in Table 1 were evaluated by automated planar patch clamp on the Patchliner® as described in Example P2.1. Table 1 shows the % effect on peak potentiation caused by 3 µM of compounds of the invention in the presence of acetylcholine. The compounds are designated either as Type I or Type II modulators based on the electrophysiology trace. Type 1 predominately affects the peak current. Type II modulators affect the peak current and also delay the desensitization of the receptor.

TABLE 1

| Example | Peak potentiation at 3 μM compound | Type I or Type II |
|---------|------------------------------------|-------------------|
| 1 | 2098% | I |
| 2 | 2290% | I |
| 3 | 2271% | II |
| 4 | 30% | I |
| 5 | 326% | I |
| 6 | 374% | I |
| 7 | 663% | I |
| 8 | 428% | I |
| 9 | 83% | I |
| 10 | 41% | I |
| 11 | 78% | I |
| 12 | 257% | I |

Compounds shown in Table 2 showed a significant effect in the mouse T-maze Continuous Alternation Task as described in Example P3. The compounds were dosed orally at 10 mg/kg.

TABLE 2

| Example | T-maze % control at 10 mg/kg |
|---------|------------------------------|
| 7 | 80% |
| 5 | 78% |
| 1 | 70% |
| 2 | 76% |
| 3 | 73% |

The invention claimed is:

1. A compound of Formula (Ib), or a pharmaceutically acceptable salt thereof:

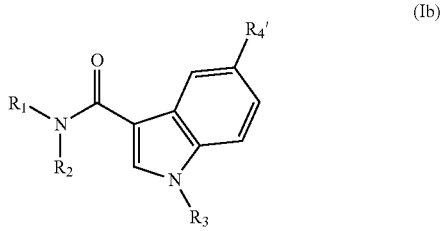

(Ib)

wherein

R$_1$ is selected from pyridine or pyrimidine, each of which is substituted with one of F or CF$_3$;

R$_2$ is selected from hydrogen or C$_1$-C$_4$ alkyl;

R$_3$ is C$_1$-C$_4$ alkyl; and

R$_4$' is selected from F, halo C$_1$-C$_4$ alkyl or halo C$_1$-C$_6$ alkoxy.

2. A compound of claim 1, wherein R$_2$ is hydrogen or methyl.

3. A compound or a pharmaceutically acceptable salt thereof, which is:

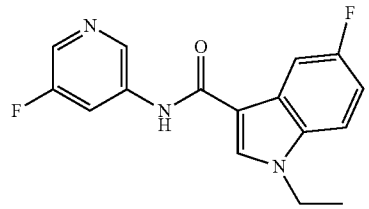

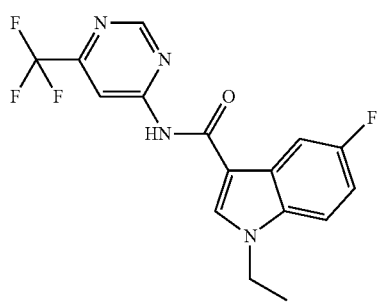

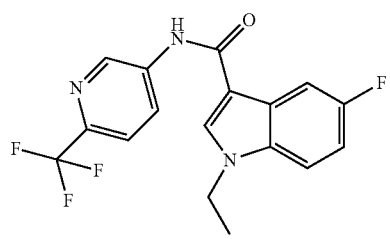

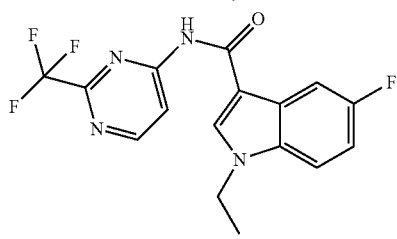

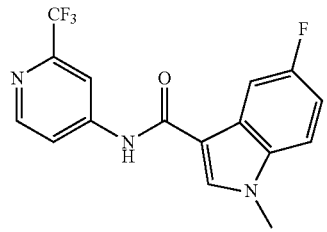

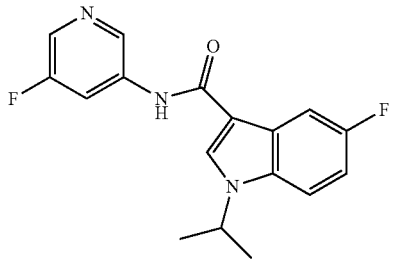

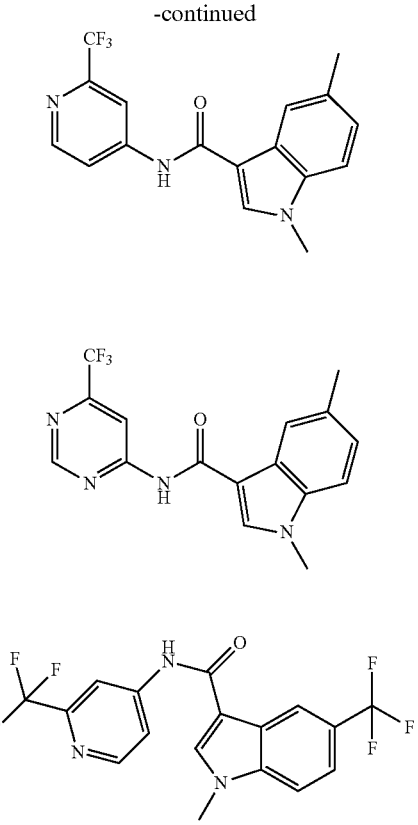
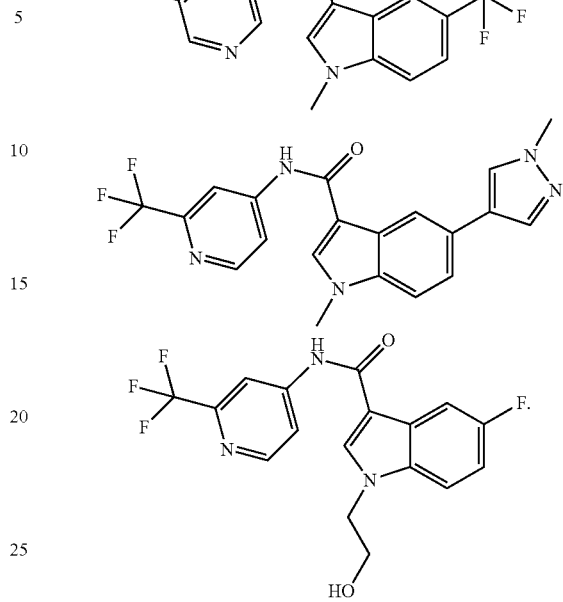
4. A composition comprising a compound of claim 1, or a pharmaceutically acceptable salt thereof and at least one pharmaceutically acceptable adjuvant, carrier or diluent.
* * * * *